United States Patent [19]
Jacobson et al.

[11] Patent Number: 5,280,015
[45] Date of Patent: Jan. 18, 1994

[54] 2-SUBSTITUTED ADENOSINES AND 2-SUBSTITUTED ADENOSINE 5'-CARBOXAMIDES

[75] Inventors: Kenneth A. Jacobson; R. Tyler McCabe, both of Silver Spring; Phil Skolnick, Potomac, all of Md.

[73] Assignee: The United States of America as represented by the Department of Health and Human Services, Washington, D.C.

[21] Appl. No.: 577,528

[22] Filed: Sep. 5, 1990

[51] Int. Cl.$^5$ .................. A61K 31/70; C07H 19/167
[52] U.S. Cl. ................................ 514/46; 536/27.22; 536/27.61
[58] Field of Search ........................ 514/46; 536/26

[56] References Cited

FOREIGN PATENT DOCUMENTS 354180 2/1990 European Pat. Off. .

OTHER PUBLICATIONS

Nikodijevic et al., *FEBS Letters*, 261(1), 67–70 (1990); *Chem. Abstr.*, 112, p. 57, Abstr. No. 191,746m (1990); only CA Abstract. supplied.
Jacobson et al., *J. Mol. Recognit.*, 2(4), 170–178 (1989); *Chem. Abstr.*, 113, p. 380, Abstr. No. 148,304z (1990); only CA Abstract supplied.
Barrington et al., *Proc. Nat. Acad. Sci. USA*, 86, 6572–6576 (Sep. 1989).
Ramkumar et al., *J. Clin. Invest.*, 82, 242–247 (1988).
R. P. Haugland, *Handbook of Fluorescent Probes and Research Chemicals*, 5th Ed., Molecular Probes, Inc., Eugene, Oreg., 1992, pp. 5–8.
Shai et al., "$^{18}$F-Labeled Insulin: A Prosthetic Group Methodology for Incorporation of a Positron Emitter into Peptides and Proteins," *Biochemistry*, 28(11), 4801–4806 (1989).

*Primary Examiner*—Johnnie R. Brown
*Assistant Examiner*—L. Eric Crane
*Attorney, Agent, or Firm*—Birch, Stewart, Kolasch & Birch

[57] ABSTRACT

The present invention is directed to compounds useful as probes for characterizing and studying the adenosine $A_2$ receptor. The present invention is also directed to methods of treating central nervous system disorders and cardiovascular disorders which include treating hypertension and thrombosis by administering said compounds.

10 Claims, 3 Drawing Sheets

2-SUBSTITUTED ADENOSINES AND 2-SUBSTITUTED ADENOSINE 5'-CARBOXAMIDES

BACKGROUND OF THE INVENTION a) Field of the Invention

The present invention is directed to compounds useful as probes for characterizing and studying the adenosine $A_2$ receptor. The present invention is also directed to methods of treating central nervous system disorders and cardiovascular disorders which include treating hypertension and thrombosis by administering said compounds.

b) Description of Related Art

Adenosine acts as a modulator of activity in the cardiovascular system, central nervous system, immune system, and other physiological systems. Adenosine receptors are subdivided into two subclasses; the $A_1$- and the $A_2$-receptors, which are in general inhibitory and stimulatory, respectively, towards adenylate cyclase.

$A_2$-adenosine receptors mediate the following physiological effects of adenosine: the inhibition of platelet aggregation, immunosuppression, vasodilation, and anti-psychotic like actions.

EP-A 354,180 discloses certain imidazo [4,5-b] pyridine derivatives which exhibit pharmacological properties as $A_2$-receptor antagonists and the preparation thereof. These compounds differ from the present compounds as the present compounds make use of a lower alkyl diamine moiety bound to a carboxy group, which is active alone or can be then derivatized with other compounds, e.g. compounds having acyl radicals which are in turn also active at the adenosine $A_2$ receptor.

SUMMARY OF THE INVENTION

The present invention is directed to a compound having the formula:

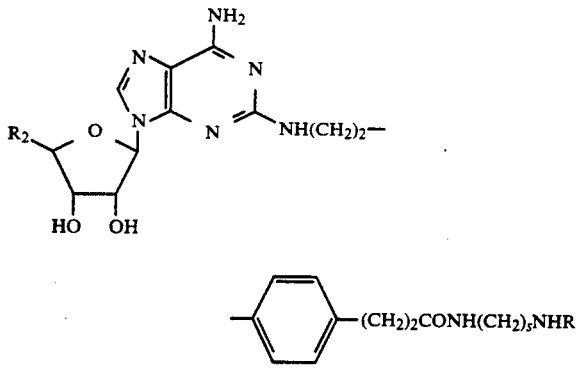

wherein
R is H, lower alkyl, lower alkenyl, an acyl radical, an isothiocyanate radical, or a reporter group; and
$R^2$ is $(CH_2)_nOH$ or $CONH(CH_2)_nH$ or $CONH$-cyclopropyl wherein n=1-4; and wherein s=1-6.

The present invention is also directed to the compounds which are reacted with a reporter group, or are radiolabeled, and which are useful in detecting adenosine-$A_2$ receptors in vivo and in vitro.

The compounds of the present invention can also be covalently bound to an affinity column matrix and thus used in a method for isolating adenosine $A_2$ receptors which, in turn, can be further utilized in studying receptor action, and used for development of other drugs which are effective and adenosine $A_2$ receptor specific.

A further aspect of the present invention is also directed to compositions containing said compounds and which are present in an effective amount and in conjunction with a pharmaceutically acceptable carrier, which can be utilized in vitro and in vivo as well.

A further aspect of the present invention is also directed to a method of treating cardiovascular disorders such as hypertension and thrombosis by administering an antihypertensive or an antithrombocytic effective amount of the compound of the present invention.

Still a further aspect of the present invention is directed to a method of treating CNS disorders such as schizophrenia by administering an antipsychotic effective amount of the compound of the present invention.

A further aspect of the present invention is directed to a method of isolating adenosine $A_2$ receptors by contacting a solution containing said receptors with a compound according to claim 16 bound to a solid support matrix, to bind said adenosine $A_2$ receptors; and collecting said bound adenosine $A_2$ receptors.

Further scope of the applicability of the present invention will become apparent from the detailed description provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The compound having the formula

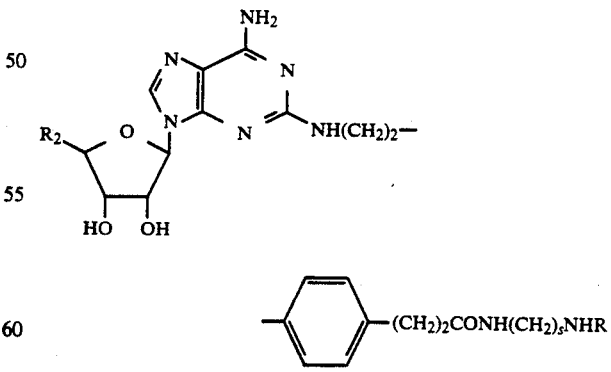

Figure 1:
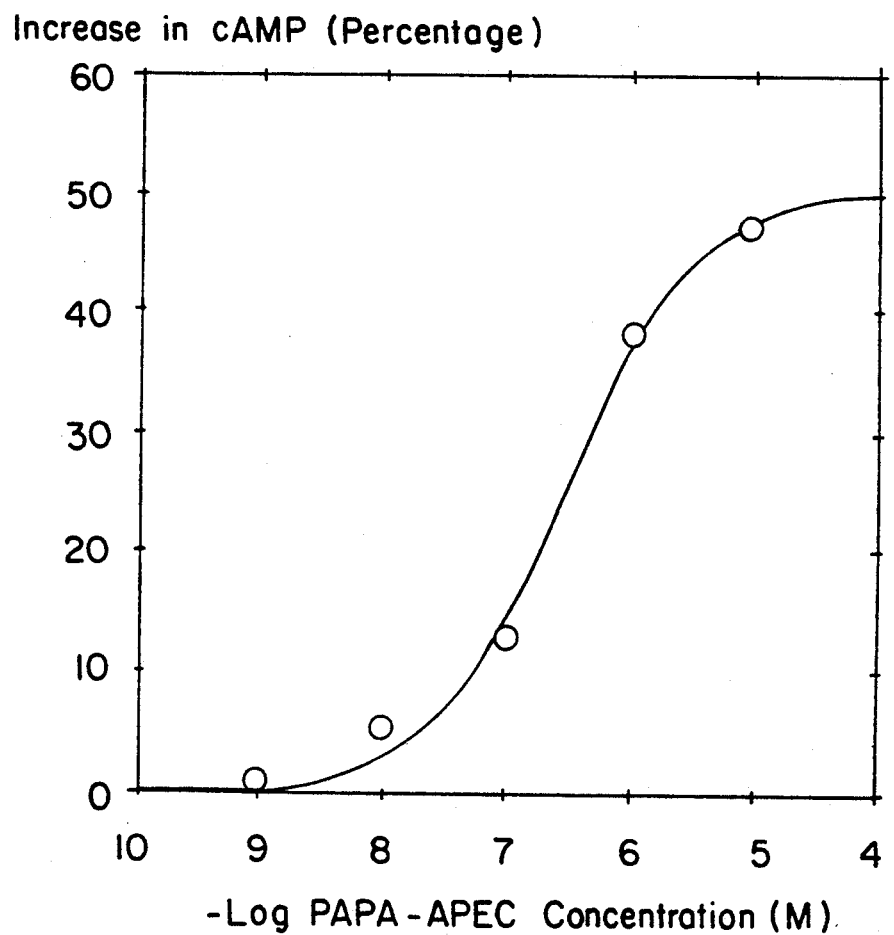
FIG. 1 is a dose dependent curve showing an increase in cAMP in human platelets produced by Compound 6, Table 1.
Figure 2:
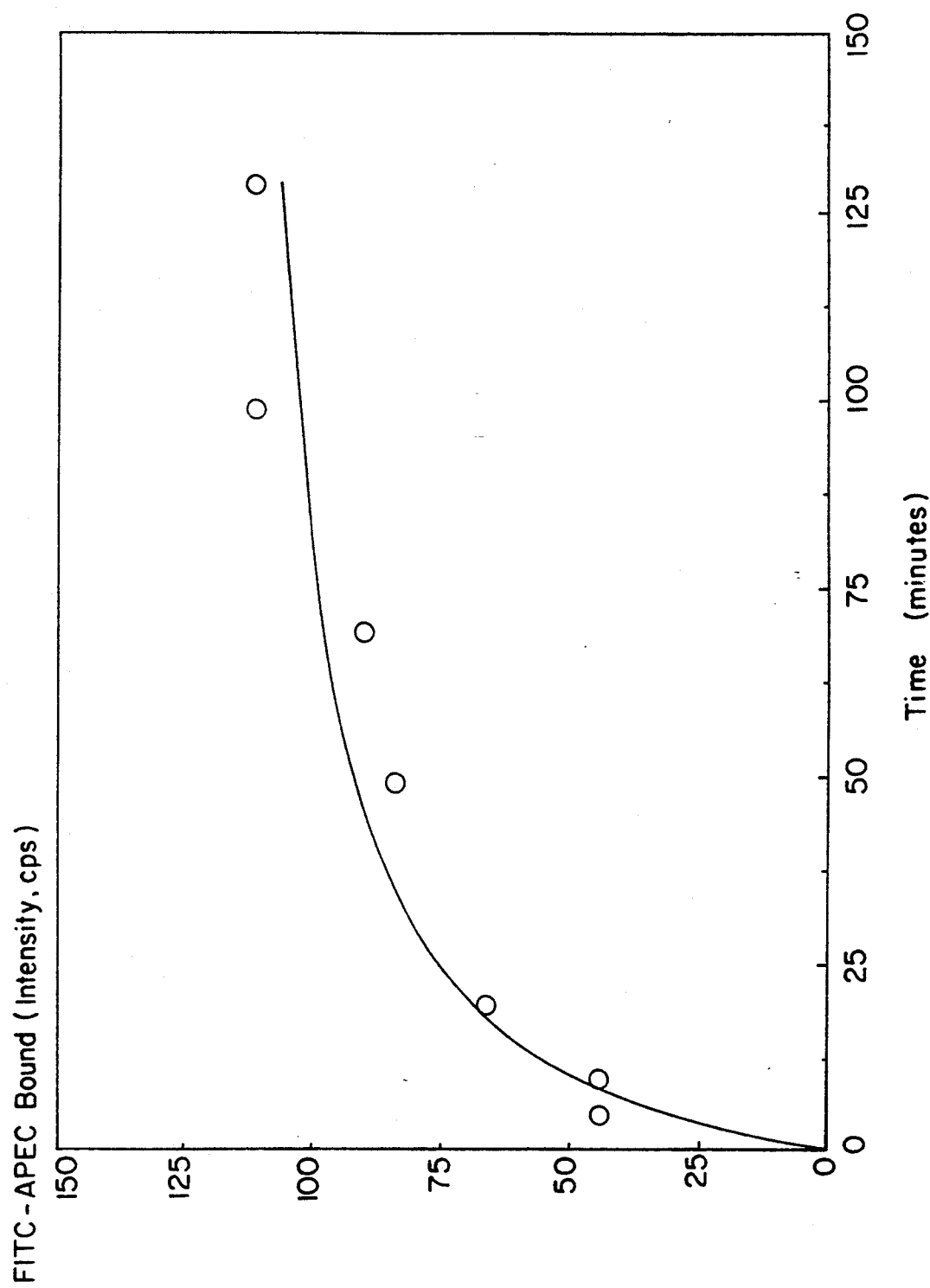
FIG. 2 is a graph depicting the association of FITC-APEC binding to membranes prepared from bovine stratum bound over time.

wherein
R is H, lower alkyl, lower alkenyl, an acyl radical, an isothiocyanate radical, or a reporter group; and
$R^2$ is $(CH_2)_nOH$ or $CONH(CH_2)_nH$ or $CONH$-cyclopropyl wherein n=1-4, and wherein s=1-6, is useful in carrying out the present invention.

The compound having the formula

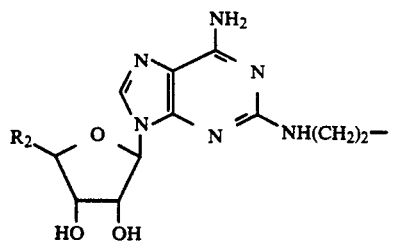

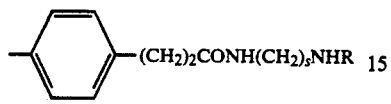

wherein
R is H; lower alkyl, lower alkenyl,

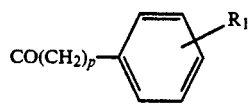

and wherein
$R_1$=OH, NH$_2$, NHCO$_2$CH$_2$C$_6$H$_5$, (CH$_2$)$_m$X, m=0–4,
X=Cl, F, or Br, and p=0–4,

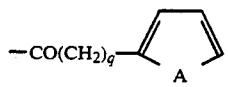

and wherein
A=O or S, and q=0–4, CO(CH$_2$)$_n$X,

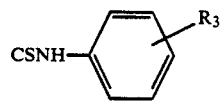

wherein
$R_3$ is NCS or SO$_3$Na; or a reporter group; and
$R_2$ is (CH$_2$)$_n$OH or CONH(CH$_2$)$_n$CH$_3$ or CONH-cyclopropyl wherein n=0–4;
is particularly useful.

The term "lower" referred to above and hereinafter in connection with organic radicals or compounds respectively defines such with up to and including 7, preferably up to and including 4 and advantageously one or two carbon atoms.

A lower alkyl group is straight chain or branched and preferably contains 1 to 4 carbon atoms, and represents, for example, methyl, ethyl, n-propyl or n-butyl.

A lower alkenyl group is a straight or branched chain alkylene and preferably contains 1 to 4 carbon atoms and represents, for example, methylene, ethylene, propylene or butylene.

The term acyl radical is any organic radical derived from an organic acid by the removal of the hydroxyl group, e.g. R—C(O)—, wherein R is any organic group so as to form an amide bond with APEC (2-[4-[2-[2-aminoethylaminocarbonyl]ethyl]phenyl]ethylamino]-5'-N-ethylcarboxamido adenosine).

The compound of the present invention also includes compounds which have as R reporter groups bound thereto.

The term reporter group includes agents which when bound to a functionalized receptor provide a means for external detection or characterization or state of binding of that receptor.

The reporter group can be detected by radiolabeling. Examples of radiolabels include, but are not limited to, $^{125}$I, $^{18}$F, $^{99}$Tc, or Chloramine T and the like or any other radioactive element capable of detection by those skilled in the art.

Some reporter groups can also be detected spectroscopically. Examples of spectroscopic detection include but are not limited to ultraviolet and visible absorption, fluorescence, electrospin resonance, nuclear magnetic resonance and the like.

Reporter groups useful in practicing the present invention include, but are not limited to, a spectroscopic reporter group, a fluorescent dye, a chemical or photochemical affinity probe, a spin label probe or an enzyme.

Spin label probes useful as reporter groups according to the present invention include, but are not limited to, 4-isothiocyanate-2,2,6,6,-tetramethyl piperidinyloxy free radical, N-(4-(iodoacetyl)amino)-2,2,6,6-tetramethylpiperidine-1-oxyl (TEMPO 1A), N-(3-(iodoacetyl)amino)-2,2,5,5-tetramethylpyrrolidine-1-oxyl (PROXYL 1A), succinimidyl 2,2,5,5-tetramethyl-3-pyrroline-1-oxyl-3-carboxylate, 2,2,5,5-tetramethyl-3-pyrroline-1-oxyl-3-carboxylic acid, and 9-doxylstearic acid.

A preferred spin label is a 4-isothiocyanate-2,2,6,6-tetramethyl piperidinyloxy free radical.

Chemical or photochemical affinity probes useful for receptor crosslinking according to the present invention include, but are not limited to, bromoacetyl, m- or p-phenylenediisothiocyanate, N-succinimidyl suberic acid, 4-azidosalicylic acid, 2-(p-azidosalicylamido)ethyl-1,3'dithiopropionic acid, 5-azido-2-nitrobenzoic acid, 2-(m-azido-o-nitrobenzamido)ethyl-1,3'dithiopropionic acid, 6-(4'-azido-2'-nitrophenylamino)hexanoate, (4-azidophenyl)-1,3'-dithiopropionic acid, 4-azidobenzoic acid, 4-azidophenylisothiocyanate, 2-diazo-3,3,3-trifluoropropionic acid.

Prosthetic groups useful as reporter groups for radiolabeling according to the present invention include but are not limited to diethylenetriaminepentacetic acid, ethylenediamine tetraacetic acid, 2-p-nitrobenzyl-1,4,7,10-tetraazacyclododecane-N,N',N'',N'''-tetraacetic acid, dimercaptosuccinate, N,N'-1,2-ethylenediyl-bis-L-cysteine diethyl ester, p-hydroxyphenylpropionic acid, p-aminobenzoic acid.

Pharmaceutical compositions useful in therapeutic treatments comprise an effective amount of the compound having the formula

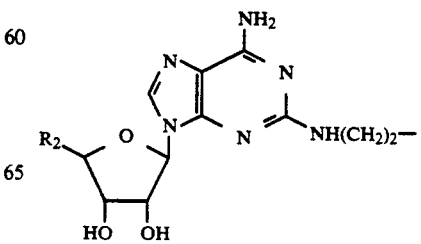

-continued

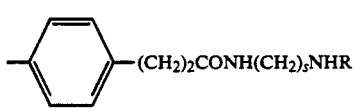

wherein
R is H, lower alkyl, lower alkenyl,

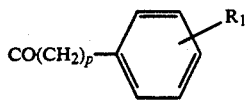

and
$R^1$ is H, OH, $NH_2$, $NHCO_2CH_2C_6H_5$, $(CH_2)_mX$
p=0–4, X=Cl, Br or F, or

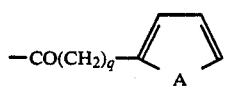

and
A is O or S, q=0–4; and
$R_2$ is $(CH_2)_nOH$ or $CONH(CH_2)_nH$ or CONH-cyclopropyl and n=0–4, or a physiologically acceptable salt thereof; and a pharmaceutically acceptable carrier.

The compound of the present invention can be administered as pharmaceutical compositions which can be used in treating cardiovascular disorders by administering to a host in need thereof, an effective amount of a compound having the formula

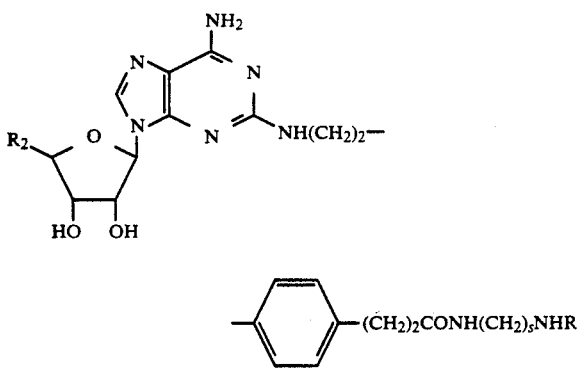

wherein
R is H, lower alkyl, lower alkenyl,

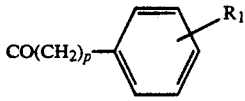

and $R^1$ is H, OH, $NH_2$, $NHCO_2CH_2C_6H_5$, $(CH_2)_mX$, m=0–4, X=Cl, Br or F, p=0–4, and

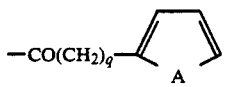

and
A is O or S, q=0–4, or $R_2$ is $(CH_2)_nOH$, or $CONH(CH_2)_nH$ or CONH-cyclopropyl and n=0–4, or a physiologically acceptable salt thereof.

Particular cardiovascular disorders which benefit from treatment with the compound of the present invention, include but are not limited to, hypertension and thrombosis.

The compound of the present invention can also be used for treating central nervous system disorders by administering to a host in need thereof, an effective amount of a compound having the formula

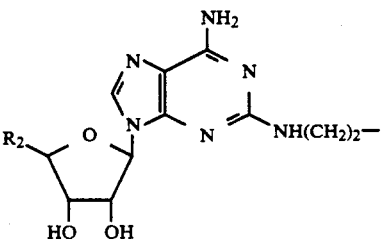

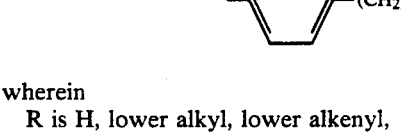

wherein
R is H, lower alkyl, lower alkenyl,

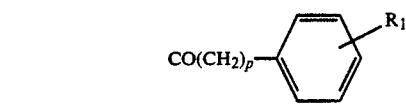

and
$R^1$ is H, OH, $NH_2$, $NHCO_2CH_2C_6H_5$, $(CH_2)_mX$, m=0–4, X=Cl, Br or F, p=0–4, and

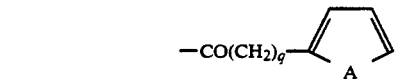

and
A is O or S, q=0–4, or
$R_2$ is $(CH_2)_nOH$, or $CONH(CH_2)_nH$ or CONH-cyclopropyl and n=0–4, or a physiologically acceptable salt thereof.

An example of a central nervous system disorder which can benefit from treatment with the compound of the present invention includes, but is not limited to, psychotic-like disorders such as schizophrenia.

The compound of the present invention is radiolabeled e.g. by mixing a solution which includes the appropriate compound with a radiolabeled prosthetic reagent capable of delivering the radioactive isotope. For example, when radiolabeled iodination is intended, the compound is mixed with, for example, $^{125}$INa and chloramine T. The radiolabeled product can then be isolated by appropriate means, for example, by HPLC.

The amounts of reactants, reagents, and reaction parameters utilized in preparing the radioactive derivatives are well within the level of skill in the art.

Examples of other prosthetic groups useful in radiolabeling the compound of the present invention, and which are not limiting, are described in Seever and Counsell, *Chem. Rev.* 1982, Vol. 82, p. 575

The compound of the present invention can also be labeled by covalently bonding said compound to a fluorescent dye by known chemical methods. The fluorescent labeled compound can then be subjected to appropriate fluorescent receptor binding assays as discussed hereinbelow for studying the adenosine $A_2$ receptors.

Fluorescent dyes which are useful as reporter groups include, but are not limited to, 5-(and 6-)-carboxynaphthofluorescein 5-(and 6-) carboxyfluorescein; 7-hydroxycoumarin-4-acetic acid; acridone-10-acetic acid; tetramethylrhodamine-5-(and-6)-isothiocyanate (TRITC); 1-pyreneisothhiocyanate; 9-acridineisothiocyanate; and 4,4'-diisothiocyanatostilbene-2,2'-disulfonic acid, disodium salt (DIDS).

The compound of the present invention can be made into appropriate physiologically acceptable salts. Physiologically acceptable salts useful in the present invention are generally acid addition salts, and are preferably of therapeutically acceptable inorganic or organic acids, such as strong mineral acids, for example hydrochloric acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicyclic, 4-aminosalicylic, palmitic, nicotinic, methanesulfonic, ethanesulfonic, hydroxyethanesulfonic, benzenesulfonic, p-toluene-sulfonic, naphthalenesulfonic, sulfanilic, cyclohexylsulfamic acid; or ascorbic acid. For compounds having a free carboxy group, physiologically acceptable salts are also derived from bases, e.g. alkali metal salts, such as the sodium salt, or salts derived from acceptable amines, such as trimethylamine.

The compounds of the present invention are active in state of the art in vitro and in vivo test systems, indicative of adenosine $A_2$ receptor agonist activity in mammals. The adenosine $A_2$ receptor agonists of the present invention are also useful in mammals including man, e.g. in the treatment of central nervous system disorders or cardiovascular disorders, and particularly in treating hypertension and thrombosis.

The compounds of the invention can be either obtained in the free form, or as a salt thereof. For example, any resulting free base can be converted into a corresponding acid addition salt, preferably with the use of a pharmaceutically acceptable acid or anion exchange preparation, or the resultant salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are then first converted into salts. In view of the close relationship between the free compounds and the compounds in the form of their salts, whenever a compound is referred to in this context, a corresponding salt is also intended, provided such is possible or appropriate under the circumstances.

The compound, including its salts, may also be obtained in the form of their hydrates, or include other solvents used for the crystallization.

The compound of the present invention includes prosthetic groups for radiolabeling, a biotin conjugate, ligands for chemical affinity labeling (bearing electrophilic groups) and photoaffinity crosslinking (aryl amines), and free radical derivative for electron spin resonance spectroscopy. The compound of the present invention includes chemically reactive chains potentially of use in anchoring the high affinity ligands to a solid support matrix for isolation of $A_2$ receptors by affinity chromatography. One aryl amine derivative was iodinated using $^{125}I$ to afford an $A_2$-selective agonist radioligand of high affinity and high specific activity.

Solid support matrices which can be used for immobilizing the compounds of the present invention include but are not limited to agarose, carboxymethylagarose, cyanogen bromide activated agarose, omegaaminoalkylaminocarboxymethyl agarose, carboxymethylcellulose, aminoethylpolyacylamide, 3-aminopropyldiethoxysilyl silica, chloromethylpolystyrene, epichlorohydrin-activated agarose, thiopropyl cyanogen bromide activated agarose, aminoalkyl cyanogen bromide activated agarose, avidin-agarose.

The following examples are intended to illustrate the invention and are not to be construed as being limitations thereon. Temperatures are given in degrees Centigrade. If not mentioned otherwise, all evaporations are performed under reduced pressure, preferably between 15 and 100 mm Hg $\triangleq$ 20–133 mbar). The structure of final products, intermediates, and starting materials is confirmed by analytical methods, e.g. microanalysis and spectroscopic characteristics (e.g. MS, IR, NMR). Abbreviations used: hexane $\triangleq$ n-hexane, ether $\triangleq$ diethylether; THF $\triangleq$ tetrahydrofuran.

The following are abbreviations of compounds used throughout the application. CGS21680=2-[4-[2-carboxyethyl]phenyl]ethylamino]-5'-N-ethylcarboxamido adenosine; NECA=5'-N-ethylcarboxamidoadenosine; PIA=$N^6$-phenylisopropyladenosine; EDAC=1-(3-dimethylaminopropyl)-3-ethylcarbodiimide hydrochloride; Chaps=3-[(3-cholamidopropyl)dimethylammonio]-1-propane sulfonate.

All amounts used in the following examples are expressed in % by weight unless otherwise stated.

The compounds of the present invention can be prepared from the starting materials CGS21680, Compound 1, and its methyl ester derivative, Compound 2, both of which can be prepared according to the procedure set forth by Hutchison et al., *J. Med. Chem.* Vol. 33, pp. 1919–1924, 1990. 1,3-Phenylene diisothiocyanate was prepared according to the procedure set forth by Stiles et al., *Mol. Pharmacol.* 34:724–728, 1988 was prepared as described.

The amine congener, APEC, compound 3, is readily acylated, with various activated carboxylic active esters containing prosthetic groups, or with isothiocyanate derivatives, e.g. aryl isothiocyanates according to recations well known in the art. The new derivatives were then assayed for activity in binding studies (Table 2).

The compounds which have been synthesized have been characterized (and resonances assigned) by 300 MHz proton nuclear magnetic resonance spectroscopy using a Varian XL-300 FT-NMR spectrometer. Unless noted, chemical shifts are expressed as ppm downfield from tetramethylsilane. Intermediates were characterized by NMR and by chemical ionization mass spectroscopy (CIMS, NH₃) using a Finnigan 1015 mass spectrometer modified with EXTREL electronics or on a Finnigan 4500 MS. The adenosine analogs were characterized additionally by plasma desorption mass spectroscopy according to the procedure of Jacobson et al, J. Chem. Soc. Perkin I, 2143–2149, 1986, and were identified by the presence of positive ion peaks observed at mass=m+23. C, H, and N analysis was carried out by Atlantic Microlabs (±0.4% acceptable). [$^3$H]N$^6$-Phenylisopropyladenosine and [$^3$H]5'-N-ethylcarboxamidoadenosine were obtained from Dupont NEN Products, Boston, Mass. N$^6$-Cyclopentyladenosine, XAC, and ADAC were obtained from Research Biochemicals, Inc., Natick, Mass.

Synthesis of Intermediates Used in Preparation of the Derivatives of the Present Invention Synthesis of 2-[4-(benzyloxycarbonylamino)phenylacetylamino]ethylamine, 22

Methyl 4-aminophenylacetate hydrochloride (1.01 g, 5.0 mmol) was acylated using carbobenzoxy chloride (0.72 ml, 5.0 mmol) in a methanol/aqueous sodium bicarbonate mixture. The product, methyl 4-(benzyloxycarbonylamino)phenylacetate, 17, was extracted into methylene chloride and isolated as an oil in quantitative yield.

Methyl 4-(benzyloxycarbonylaminophenyl)acetate (compound 21, 1.3 g, 4.3 mmol) was treated with ethylenediamine (4 ml) and heated at 50° C. for 10 min. Several cycles of evaporation under vacuum and addition of methanol left an oil which could be crystallized from methanol/ether. Yield 0.80 g (56% yield), mp 186–190° C. C, H, and N analysis was correct for the 3/2 hydrate.

Synthesis of N-succinimidyl 3-(benzyloxycarbonylamino)benzoate, 20 m-Aminobenzoic acid (2.94 g, 21 mmol) was suspended in 50 ml of methanol and treated with carbobenzoxy chloride (3.0 ml, 21 mmol). The mixture was sonicated for 10 min and water was added resulting in the crystallization of the product, 3-(benzyloxycarbonylamino)benzoic acid, (mp 218–219° C.), obtained in 67% yield. C, H, and N analysis: calc. 66.41% C, 4.83% H, 5.16% N; found 66.30% C, 4.82% H, 5.20% N.

(3-benzyloxycarbonylamino)benzoic acid, 0.30 g, 1.1 mmol), N-hydroxysuccinimide (0.30 g, 2.6 mmol), and EDAC (0.36 g, 1.9 mmol) were combined in 10 ml DMF. After being stirred for 12 hours, the reaction mixture was treated with water and ethyl acetate. The organic layer was separated, washed (0.1M HCl/1M bicarbonate), and evaporated leaving the product (mp 110–115° C.) in 89% yield. C, H, and N analysis calc. 61.95% C, 4.38% H, 7.61% N; found 61.79% C, 4.38% H, 7.67% N.

EXAMPLE 1

Synthesis of 2-[4-[2-[2-aminoethylaminocarbonyl]ethyl]phenyl]ethylamino]-5'-N-ethylcarboxamido adenosine, (Compound 3, Table 1) (APEC)

Compound 2 (100 mg, 0.195 mmol) was dissolved in ethylene diamine and heated at 50° C. for 12 hours. The solvent was evaporated under a stream of nitrogen. Methanol and ether were added to give an oily precipitate, which solidified in vacuo. A solid was obtained by dissolving in methanol and reprecipitating with ether. The amorphous solid (yield 96 mg, 91%) melted at 113–117° C. Characteristic $^1$H, aromatic, C-8); 7.75 (m, 1H, NH to 1° amine); 7.11 (m, 4H, phenyl ring); 5.83 (d, 1H, J=6.3 Hz, ribose C$_1$'); 4.71, 4.24, and 4.17, (each 1H, ribose); 3.00 (m, 2H, CH$_2$ β to 1° amine); 2.7 (m, 4H, α to phenyl ring); 2.33 (t, 2H, J=7 Hz, CH$_2$ α to CO); and 0.96 (t, J=7 Hz, CH$_3$).

Compounds which are acylated with the derivative APEC, Compound 3, Table I, can be produced according to the general reaction scheme as follows.

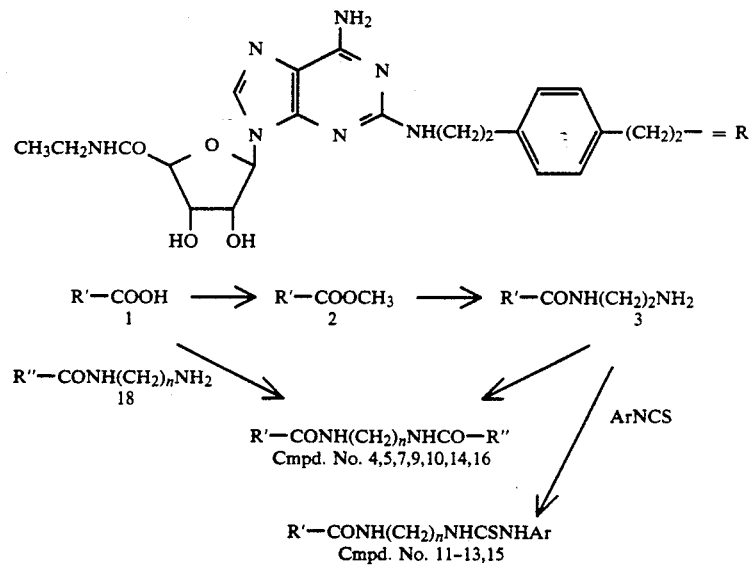

R'—COOH ⟶ R'—COOCH$_3$ ⟶ R'—CONH(CH$_2$)$_2$NH$_2$
   1              2                 3

R'''—CONH(CH$_2$)$_n$NH$_2$
         18

R'—CONH(CH$_2$)$_n$NHCO—R''
Cmpd. No. 4,5,7,9,10,14,16

ArNCS

R'—CONH(CH$_2$)$_n$NHCSNHAr
Cmpd. No. 11–13,15

APEC (Compound 3, Table 1, 10 μmol) was dissolved in 0.5 ml of dimethylformamide or in a 1:1 mixture of isopropanol/acetonitrile. To form amides, an active ester (20 μmol) was added. To form thioureas (compds. 11–13, and 15), the appropriate isothiocyanate derivative (20 μmol, or 50 μmol if bifunctional) was added. The reaction is followed by TLC, and generally is complete within several minutes. The solvent is evaporated under a stream of nitrogen. Acetonitrile and ether are added causing the product to precipitate. The product is recrystallized sequentially from DMF/acetonitrile/ether and from methanol/ether.

EXAMPLE 2

2-[4-[2-[2-[3-[4-(Hydroxy)phenyl]propionylamino]ethylaminocarbonyl]ethyl]phenyl]ethylamino]-5'-N-ethylcarboxamidoadenosine, (Compound 4, Table 1)

APEC (2.0 mg) was dissolved in 0.4 ml of methanol. N-Sulfosuccinimidyl 3-[4-(hydroxy)phenyl]-propionate (7 mg) was added. The reaction was followed by TLC, and generally was complete within one hour. The volume was reduced under a stream of nitrogen, and water was added resulting in a fine precipitate. The mixture was centrifuged, and the precipitate was collected and washed with a minimum of water. Dried in vacuo to give 2.1 mg of chromatographically pure product. The 300 MHz $^1$H-NMR spectrum was consistent with the assigned structure.

EXAMPLE 3

2-[4-[2-[2-[[2-Thiophenacetyl]propionylamino]ethylaminocarbonyl]ethyl]phenyl]ethylamino]-5'-N-ethylcarboxamidoadenosine, (Compound 5, Table 1)

N-Succinimidyl thiophene-2-acetic acid was prepared from equimolar quantities of thiophene-2-acetic acid, N-hydroxysuccinimide and dicyclohexylcarbodiimide in 10% dimethylformamide/ethyl acetate (recrystallized from ethyl acetate/hexanes) in 74% yield, mp 127–128° C. CHN analysis: calc. 50.20% C, 3.79% H, 5.85% N; found 50.19% C, 3,79% H, 5.82% N.

APEC (7.8 mg) was dissolved in 0.5 ml of dimethylformamide and treated with N-succinimidyl thiophene-2-acetic acid (10.1 mg). The volume was reduced at 50° C. under a stream of nitrogen. Acetonitrile and ether were added causing the product (9.2 mg, mp 116–120° C.) to precipitate.

EXAMPLE 4

Synthesis of 2-[4-[2-[2-[(4-aminophenyl)methylcarbonylamino]ethylaminocarbonyl]ethyl]phenyl]ethylamino]-5'-N-ethylcarboxamido adenosine, (Compound 6, Table 1)

Compound 7 (4.0 mg, 4.9 µmol) and 5% palladium on charcoal (Engelhard, Edison, N.J., 3 mg) were added to 0.3 ml of an equivolume mixture of methanol, dimethylformamide, and acetic acid. The mixture was hydrogenated at 40 p.s.i. for six hours. The catalyst was removed by centrifugation. The title compound was isolated in 68% yield as a white solid (2.3 mg). An additional purification by preparative TLC (silica, chloroform:methanol:acetic acid, 70:25:5) was necessary.

EXAMPLE 4a

Radioiodination of 2-[4-[2-[2-[(4-aminophenyl)methylcarbonylamino]ethylaminocarbonyl]ethyl]phenyl]ethylamino]5'-N-ethylcarboxamidoadenosine (Compound 6)

Ten µl of a solution of compound 6 (0.1 mg/ml) in methanol was placed in a microcentrifuge tube and dried completely under a stream of nitrogen. The residue was dissolved in 30 l of 0.5M Na$_2$HPO$_4$ (pH 7.35) and mixed well with 1.5 mCi of $^{125}$INa. The reaction was initiated by the addition of 10 µl of aqueous chloramine T (1 mg/ml), and the entire reaction mixture was mixed by pipette aspiration for 4 min. The reaction was terminated by the addition of 10 µl of aqueous sodium metabisulfite (2 mg/ml). The product, $^{125}$I-PAPA-APEC, was purified by HPLC. The separation was carried out on a Waters HPLC apparatus utilizing a C$_{18}$-µBondapak column and a mobile phase consisting of methanol and 20 mM ammonium formate at pH 8.1. A shallow concave gradient pattern (curve #8 on Waters model 680 Automated Gradient Controller) was used. The percent methanol was varied from 60% at zero time to 50% after 10 min, with the remainder being ammonium formate solution. The flow rate was 1.0 ml/min, and the UV detector (254 nm) was set on the 0.1 absorbance unit scale. Four major absorbance peaks (FIG. 3) were detected at retention times of approximately 4 minutes (two peaks), 5 minutes (peak A), and 7 minutes (peak B) after injection. Unreacted compound 6 (peak A) and $^{125}$I-PAPA-APEC (peak B) were identified by TLC on silica plates, in which the mobile phase consisted of a chloroform/methanol/acetic acid mixture in the ratio 85/10/5. The $R_f$ values of compound 6 and Iodinated product were 0.11 and 0.23, respectively. Peak B was the only radioactive fraction to display specific binding and the appropriate A$_2$ receptor pharmacology. A small radioactive contaminant was seen at approximately 6.5 min, but was distinguished from $^{125}$I-PAPA-APEC by an $R_f$ value of 0.36.

EXAMPLE 5

Synthesis of 2-[4-[2-[2-[[4-(benzyloxycarbonylamino)phenyl]methylcarbonylamino]ethylaminocarbonyl]ethyl]phenyl]ethylamino]-5'-N-ethylcarboxamidoadenosine, (Compound 7, Table 1)

2-[4-[2-Carboxyethyl]phenyl]ethylamino]-5'-N-ethylcarboxamido adenosine sodium salt (CGS21680C, 7.2 mg, 13 µmol) was suspended in 0.5 ml of dimethylformamide and treated with 1-hydroxybenzotriazole (20 mg) and 1-ethyl-3-(3-dimethylaminopropyl)carbodiimide hydrochloride (13 mg, 68 µmol). The mixture was stirred for several minutes and treated with 2-[[4-(benzyloxycarbonyl)amino]phenylacetylamino]ethylamine (compound 22, 5.5 mg, 17 µmol). After 24 hours, water (4 ml) was added and a precipitate was separated by centrifugation, washed with water, and dried at 50° C. in vacuo. The title compound was obtained in 65% yield (7.0 mg), and was shown to be homogeneous by thin layer chromatography ($R_f$=0.18 on silica, chloroform/methanol/acetic acid, 85:10:5). The 300 MHz $^1$H-NMR spectrum was consistent with the assigned structure.

EXAMPLE 6

2-[4-[2-[2-[3-Aminobenzoylamino]ethylaminocarbonyl]ethyl]phenyl]ethylamino]5'-N-ethylcarboxamido adenosine, (Compound 8, Table 1)

Compound 9 (4.2 mg) and 5% palladium on charcoal (Engelhard, Edison, N.J., 3 mg) were added to 0.3 ml of an equivolume mixture of methanol, dimethylformamide, and acetic acid. The mixture was hydrogenated at 25 p.s.i. for 16 hours. The catalyst was removed by centrifugation. The title compound was isolated in 68% yield as a white solid (3.1 mg).

EXAMPLE 7

2-[4-[2-[2-[3-(Benzyloxycarbonylamino)benzoylamino]ethylaminocarbonyl]ethyl]phenyl]ethylamino]-5'-N-ethylcarbox-amidoadenosine, (Compound 9, Table 1)

2-[4-[2-Carboxyethyl]phenyl]ethylamino]-5'-N-ethylcarboxamido adenosine sodium salt (CGS21680C, 14.4 mg) was suspended in 1 ml of dimethylformamide and treated with 1-hydroxybenzotriazole (20 mg) and 1-ethyl-3-(3-dimethylamino-propyl)carbodiimide hydrochloride (20 mg). The mixture was stirred for several minutes and treated with 2-[[3-(benzyloxy-carbonyl-)amino]benzoylamino]ethylamine trifluoroacetate (compound 22, 15 mg, 46 µmol) and 20 µl of diisopropylethylamine. After 24 hours, water (5 ml) was added and a precipitate was separated by centrifugation, washed with water, and dried at 50° C. in vacuo. 7.4 mg of the title compound was obtained, and was purified to homogeneity by thin layer chromatography (R$_f$=0.20 on silica, chloroform/methanol/acetic acid, 85:10:5).

Alternately, APEC (7.1 mg) was dissolved in 0.5 ml of dimethylformamide. An active ester (N-succinimidyl 3-(benzyloxycarbonylamino)benzoate, 10 mg) was added. The crude product was recrystallized from methanol to yield 7.3 mg of pure product.

EXAMPLE 8

2-[4-[2-[2-[3-Biotinylamino]-ethylaminocarbonyl]ethyl]phenyl]ethylamino]-5'-N-ethylcarboxamidoadenosine. (Compound 10, Table 1)

APEC (3.0 mg) was dissolved in 0.2 ml of dimethylformamide. An active ester (N-succinimidylbiotin, 4.0 mg) was added. The reaction was stirred overnight. The solvent was evaporated under a stream of nitrogen. Methanol and ether were added causing the product to precipitate. A total of two crops of the product were collected to yield 3.5 mg. The product was pure by thin layer chromatography (silica, chloroform:methanol:acetic acid, 85:10:5, Rf—0.09).

EXAMPLE 9

2-[4-[2-[2-[3-(Isothiocyanatophenylthioureido)]-ethylaminocarbonyl]ethyl]phenyl]ethylamino]-5'-N-ethylcarboxamidoadenosine, (Compound 11, Table 1)

APEC (10 mg, 18.4 µmol) was suspended in a mixture of 0.1 ml of isopropanol and 0.2 ml dimethylformamide. 1,4-Phenylenediisothiocanate (12 mg) was added with agitation and a solution formed after several minutes. The volume was reduced under a stream of nitrogen, and ether was added causing the product to precipitate. The product (6.4 mg) was pure by thin layer chromatography (silica, chloroform:methanol:acetic acid, 70:25:5, Rf=0.49). In the same TLC system APEC had an Rf of 0.28.

EXAMPLE 10

2-[4-[2-[2-[3-(Isothiocyanatophenylthioureido)]-ethylaminocarbonyl]ethyl]phenyl]ethylamino]-5'-N-ethylcarboxamidoadenosine, (Compound 12, Table 1)

Compound 12 (the 4-isothiocyanato isomer) was prepared similarly from 1,4-phenylenediisothiocanate and APEC in a 1:1 mixture of acetonitrile:isopropanol. The product was pure by thin layer chromatography.

EXAMPLE 11

2-[4-[2-[2-[4-(Sulfophenylthioureidyl)]-ethylaminocarbonyl]ethyl]phenyl]ethylamino]-5'-N-ethylcarboxamidoadenosine sodium salt, (Compound 13, Table 1)

APEC (2.7 mg) was dissolved in 0.3 ml of dimethylformamide and treated with 1.7 mg of 4-sulfophenylisothiocyanate sodium salt. The reaction was followed by TLC, and was complete within several minutes. The solvent was evaporated under a stream of nitrogen. The residue was recrystallized from methanol/ether to yield 2.8 mg of chromatographically pure product. The product melted broadly at 220° C.

EXAMPLE 12

2-[4-[2-[2-[2-Bromoacetylamino]ethylaminocarbonyl]ethyl]phenyl]ethylamino]-5'-N-ethylcarboxamidoadenosine, (Compound 14, Table 1)

APEC (4 6 mg) was dissolved in 0.3 ml of dimethylformamide and treated with 5 mg of bromoacetic anhydride. After several minutes, ether was added, and the resulting precipitate was recrystallized from methanol/ether to yield 3.8 mg of chromatographically pure product. The 300 MHz $^1$H-NMR spectrum was consistent with the assigned structure. The product melted with decomposition at 218-220° C.

EXAMPLE 13

2-[4-[2-[2-[4-(2,2,6,6-Tetramethylpiperidinyloxy)thioureidyl]-ethylaminocarbonylcarboxyl-amidoadenosine, Compound 15, Table 1)

APEC (5.2 mg. 9.6 µmol) was dissolved in 0.5 ml of 1:1 acetonitrile:isopropanol and treated with 2.7 mg (12.3 µmol) of 4-isothiocyanato-2,2,6,6-tetramethylpiperidinyloxy free radical (TEMPO isothiocyanate, Aldrich Chemical Co., Milwaukee, Wis.). After 24 hours, the solvent was evaporated under a stream of nitrogen. Acetonitrile and ether were added causing the product to precipitate. The product was recrystallized from DMF/acetonitrile/ether to yield 5.0 mg. The product melted broadly at 170–180° C.

EXAMPLE 14

2-[4-[2-[4-[4-(Fluoromethyl)benzoylamino]-butylaminocarbonyl]ethyl]phenyl]ethylamino]-5'-N-ethylcarboxamidoadenosine, (Compound 16, Table 1)

CGS21680 (11.5 mg, compound 1, sodium salt) and 4-(4-fluoromethylbenzoylamino)butaneamine trifluoroacetate (Sahi et al, Biochemistry, 1989, vol. 28, pp 4801–4806) were dissolved in 1.0 ml dimethylformamide and treated with 1-hydroxybenzotriazole (10 mg) and 1-ethyl-3-(3-dimethylaminopropyl)carbodiimide hydrochloride (10 mg). The mixture was stirred for ten minutes and treated with 20 µl diisoproylethylamine. After one hour, water was added resulting in 12.3 mg of product. The product was nearly pure by thin layer chromatography (silica, chloroform:methanol:acetic acid, 85:10:5, Rf=0.27). The product melted broadly at 150° C., and was recrystallized from DMF/acetonitrile/ether.

EXAMPLE 15

2-[4-[2-[2-[4-[(7-Nitrobenzo-2-oxa-1,3-diazole)amino)-]ethyl-aminocarbonyl]ethyl]phenyl]ethylamino]-5'-N-ethylcarboxamidoadenosine, (Compound 17, Table 1)

APEC (17 mg) was dissolved in 1 ml of dimethylformamide and treated with 13 mg of 4-chloro-7-nitrobenzo-2-oxa-1,3-diazole (NBD chloride). After 24 hours, the solvent was evaporated under a stream of nitrogen. Acetonitrile and ether were added causing the product to precipitate. The product was recrystallized from DMF/acetonitrile/ether to yield 8.0 mg of pure product.

EXAMPLE 16

2-[4-[2-[2-[1,3-Dihydro-1,1-bis(4-hydroxyphenyl)-3-oxo-5-isobenzofuranthioureidyl]ethylaminocarbonyl]ethyl]phenyl]ethylamino]-5'-N-ethylcarbox-amidoadenosine, (Compound 18, Table 1)

APEC (6.5 mg, 11.1 μmol) was dissolved in 0.5 ml of 1:1 acetonitrile:isopropanol and treated with 4.8 mg (12.3 μmol) of fluorescein isothiocyanato (Isomer I, Aldrich Chemical Co., Milwaukee, Wis.). After 24 hours, the solvent was evaporated under a stream of nitrogen. Acetonitrile and ether were added causing the product to precipitate. The product was recrystallized from DMF/acetonitrile/ether to yield 6.0 mg (58% yield). The 300 MHz $^1$H-NMR spectrum and Cf plasma desorption mass spectrum were consistent with the assigned structure.

The product was also synthesized via carbodiimide coupling of compound 1 (CGS21680) to 5-((2-aminoethyl)thioureidyl)fluorescein (Molecular Probes, Inc., Eugene, Ore.) in dimethylformamide.

The product was purified to >99% purity by reverse phase high pressure liquid chromatography, using a 20 minute gradient of 0% to 80% acetonitrile in water (both containing 0.1% trifuoroacetic acid), using a Vydac Protein C4 column (25×0.4 cm). 100 μl of a millimolar solution in dimethylsulfoxide was applied for each purification run. Larger quantities were readily purified on a semipreparative column. The retention time for the product was 14.1 minutes. APEC (the starting material) was shown to be >94% pure, with a retention time of 10.8 minutes. Concentration of the probe in aqueous solution (pH 7) was calculated using an extinction coefficient of 67,200 at the λmax of 490.5 nm. A quantum yield of 15.7% was observed at that wavelength.

The following is a table which lists exemplary compounds of the present invention.

TABLE 1

Structures of 2,5'-di-substituted adenosine derivatives synthesized and their characterization by Californium plasma desorption mass spectroscopy.

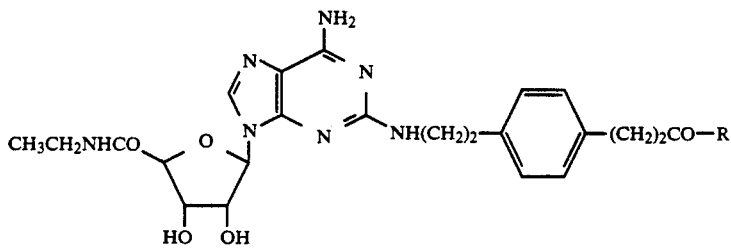

| | R = | % Yield | MS Peaks |
|---|---|---|---|
| 1 | —OH (CGS21680) | — | 544 (M + Na$_2$—H$^+$), 522$^a$, 393$^c$, 371$^c$ |
| 2 | —OCH$_3$ | — | 536$^a$, 514$^b$, 341$^c$, 336, 163 |
| 3 | —NH(CH$_2$)$_2$NH$_2$ (APEC) | 91 | 564$^a$, 542$^b$, 369$^c$, 336, 163 |
| 4 | —NH(CH$_2$)$_2$NHCO(CH$_2$)$_2$—C$_6$H$_4$—OH | 82 | 712$^a$, 690$^b$, 539$^c$, 517$^c$, 336, 163 |
| 5 | —NH(CH$_2$)$_2$NHCOCH$_2$—(2-thienyl) | 96 | 689$^a$, 667$^b$, 163 |
| 6 | —NH(CH$_2$)$_2$NHCOCH$_2$—C$_6$H$_4$—NH$_2$ | 68 | 697$^a$, 546$^c$, 524$^c$, 163 |
| 7 | —NH(CH$_2$)$_2$NHCOCH$_2$—C$_6$H$_4$—NHCO$_2$CH$_2$C$_6$H$_5$ | 65 | 831$^a$, 809$^b$, 658$^c$, 336 |
| 8 | —NH(CH$_2$)$_2$NHCO—C$_6$H$_4$(NH$_2$) | 87 | 697$^b$ |
| 9 | —NH(CH$_2$)$_2$NHCO—C$_6$H$_4$(NHCO$_2$CH$_2$C$_6$H$_5$) | 70 | 817$^a$, 795$^b$, 336, 163 |

TABLE 1-continued

Structures of 2,5'-di-substituted adenosine derivatives synthesized
and their characterization by Californium plasma desorption mass spectroscopy.

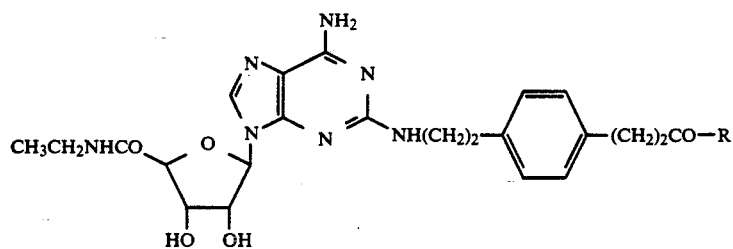

| | R = | % Yield | MS Peaks |
|---|---|---|---|
| 10 | —NH(CH$_2$)$_2$NHCO(CH$_2$)$_4$— [tetrahydrothiophene with cyclic urea] | 82 | 791[a], 769[b] |
| 11 | —NH(CH$_2$)$_2$NHCSNH—[phenyl]—NCS (meta) | 47 | 756[a], 734[b], 724 (M + Na—S), 702 (M + H$^+$—S) |
| 12 | —NH(CH$_2$)$_2$NHCSNH—[phenyl]—NCS (para) | 44 | 734[b], 702 |
| 13 | —NH(CH$_2$)$_2$NHCSNH—[phenyl]—SO$_3$Na | 85 | 802[a], 764[c] |
| 14 | —NH(CH$_2$)$_2$NHCOCH$_2$Br | 57 | 685[a] |
| 15 | —NH(CH$_2$)$_2$NHCSNH—[tetramethylpiperidine N—O] | 69 | 724 (M + H—S), 564, 550[c], 336, 163 |
| 16 | —NH(CH$_2$)$_4$NHCO—[phenyl]—CH$_2$F | 81 | 728[a], 706[b], 555[c], 534[c], 336, 163, 130 |
| 17 | —NH(CH$_2$)$_2$NH—[benzofurazan]—NO$_2$ | 84 | 728[a], 706[b], 336, 163 |

TABLE 1-continued

Structures of 2,5'-di-substituted adenosine derivatives synthesized and their characterization by Californium plasma desorption mass spectroscopy.

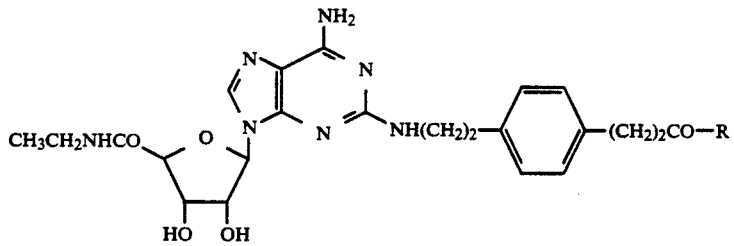

| R = | % Yield | MS Peaks |
|---|---|---|
| 18 ![structure with CO2H, NH(CH2)2NHCSNH-phenyl-fluorescein-like group, OH] | 58 | 921 (M + H—S + Na+), 899 (M + H—S), 726[c], 163 |

[a] M + Na+
[b] M + H+
[c] loss of 173 (5'-N-ethylcarboxamidoribose) from M + Na+, M + H+ —S, or from M + Na₂—H+

EXAMPLE 17

Biochemical Assays

Radioligands ([³H]PIA, [³H]NECA, and [³H]CGS21680) were obtained from DuPont NEN Products, Boston, Mass.). Stock solutions of representative compounds of the present invention in the millimolar concentration range in dimethylsulfoxide were prepared for the binding assays. The solutions were diluted as necessary and were stable to storage in the frozen state. For each assay at either the A₁ or the A₂ receptors, inhibition of binding by a range of concentrations of xanthines was assessed in triplicate in at least three separate experiments. Protein was determined using the BCA (based on the complex with cuprous ions and bicinchoninic acid) protein assay reagents purchased from Pierce Chemical Co., Rockford, Ill. Increase in cyclic AMP in human platelets was measured using the method of Newman et al., *J. Clin. Invest.*, 61:395-402, 1978.

Competitive Binding Assay in Rat Brain Using [³H]PIA, [³H]CGS21680, and [³H]NECA Inhibition of binding of 1 nM [³H]N⁶-phenylisopropyladenosine (specific activity 42.5 Ci/mmol) to A₁-adenosine receptors in rat cerebral cortex membranes was assayed as described by Jacobson et al., *Biochem. Pharmacol.* 10:1697-1707, 1987. Inhibition of binding by a range of concentrations of each compound tested was assessed in triplicate in at least three separate experiments. At least seven different concentrations spanning three orders of magnitude, adjusted appropriately for the IC₅₀ of each compound, were used. IC₅₀ values, computer-generated using a non-linear regression formula on the GraphPAD program (Institute for Scientific Information), were converted to K$_i$ values using a K$_D$ value for [³H]PIA of 1.0 nM (Jacobson, et al., 1987, supra) and the Cheng-Prusoff equation as discussed in Cheng et al., *Biochem. Pharmacol.* 22:3099-3108, 1973.

Affinity at rat striatal A₂-receptors was measured by two methods, using either [³H]NECA or [³H]CGS21680. Inhibition of binding of [³H]N-ethyl-carboxamidoadenosine (specific activity 18 Ci/mmol) to A₂-adenosine receptors in rat striatal membranes was measured as described in Bruns et al. *Mol. Pharmacol.* 29:331-346, 1986, except that 5 mM theophylline was used to define non-specific binding. N⁶-Cyclopentyladenosine was present at 50 nM to inhibit binding of the ligand at A₁-adenosine receptors. IC₅₀-values were converted to K$_i$-values as described by Bruns et al., 1986, supra).

Use of [³H]CGS21680 (specific activity 48.1 Ci/mmol) as an A₂ radioligand precluded the need for adding N⁶-cyclopentyladenosine (Hutchison, et al, 1989, supra). Rat striatum was homogenized in 25 volumes of ice cold 50 mM Tris, adjusted to pH 7.4 with hydrochloric acid, containing 10 mM magnesium chloride using a polytron (Kinematica, Gmbh., Luzerne, Switzerland) at a setting of 2-3 for 10 sec. The membrane suspension was then centrifuged at 37,000×g for 20 min at 4° C. The pellet was resuspended in buffer containing 2 IU/ml adenosine deaminase, Type VI from calf intestinal mucosa (Sigma, St. Louis, Mo.) to 20 mg/ml original tissue weight and incubated at 37° C. for 30 min. The membrane homogenate was recentrifuged as before, and the pellet was stored frozen at −70° C. until use.

For competitive binding assays using [³H]CGS21680, a volume of 1 ml was used in each 13×100 mm glass tube. The unlabeled competing ligand or 2-chloroadenosine, for determination of non-specific binding, was dissolved in 25 μl of DMSO. To this solution was added 50 μl of 200 mM MgCl$_2$, 725 μl of 50 mM Tris at pH 7.4 at room temperature, 100 μl of radioligand to produce a final concentration of 5 nM. Finally 100 μl of a striatal tissue suspension (final concentration of 150-200 μg protein per ml) was added. The mixture was incubated with shaking for 90 min at 24° C. The samples were filtered on a Brandel Cell Harvester (Brandel, Gaithersburg, Md.) with Whatman GF/B filters, and washed rapidly twice with 5 ml of ice cold 50 mM Tris, pH 7.4. Each filter disc was added to 4 ml of scintillation fluid, vortexed, and counted after 6 hours.

Competitive Binding Assay in Bovine Brain Using $^{125}$I-PAPA-APEC

Bovine striatal membranes were prepared as described (Barrington et al., Proc. Natl. Acad. Sci., 1989). 150 μl of striatal membranes (approximately 0.5 mg protein/ml, suspended in 50 mM HEPES buffer at pH 7.2, containing 10 mM MgCl$_2$) were combined with 50 μl of the indicated competitor and 50 μl of $^{125}$I-PAPA-APEC to yield a final concentration of radioligand of 1 nM. After a one hour incubation at 37 ° C., the mixture was filtered rapidly over #32 Schleicher & Scheull glass fiber filters, which had been pretreated for one hour with 0.3% polyethyleneimine. The filters were washed with three × 3 ml aliquots of pH 7.2 buffer containing 50 mM HEPES, 10 mM Mg$^{+2}$, and 0.05% CHAPS. The filters were placed in polypropylene tubes and counted in a Packard gamma counter.

The small quantities synthesized and high molecular weights necessitated the use of high field NMR and californium plasma desorption mass spectroscopy (Jacobson et al., 1986, supra) for characterization of the homogeneous products. The mass spectra (Table 1) for positive ions show either the $(M+H)^+$ or $(M+Na)^+$ ions, or peaks resulting from the loss of the 5'-N-ethyl-carboxamidoribose moiety. Thiourea derivatives, obtained from reaction of APEC with isothiocyanates and model compounds for comparison, tended to lose sulfur, during measurement of mass spectra. As was observed previously, some of the mass spectra showed the sodium replacement ion of the sodium salt, $(M+2Na—H)^+$.

Radioactive Probes

Towards the goal of radioiodination of functionalized congeners, both phenolic prosthetic groups (Jacobson et al., J. Med. Chem. 28:1341-1346, 1985), such as p-hydroxyphenylpropionic acid (Bolton-Hunter group), and aryl amine-containing prosthetic groups (Stiles et al., Mol. Pharmacol. 32:184-188, 1987), such as p-aminophenylacetic acid (PAPA) have been utilized. An additional prosthetic group for iodination, a 2-substituted thienyl group, which does not contain a hydroxyl or amino group, has been shown to iodinate readily (and selectively in the presence of phenols) via its easily-formed mercury adduct (Jacobson et al., J. Med. Chem. Vol. 32, pp. 1873-1879, 1989(a)). Thus, the p-hydroxyphenylpropionyl-, 4, 2-thienylacetyl-, 5, and p-aminophenylacetyl-, 6, derivatives of APEC were synthesized as radioiodination substrates (FIG. 1). Compounds 4 and 5 were synthesized via the direct acylation of APEC. Compound 6 was synthesized via the condensation of the carboxylic acid CGS21680 with the appropriate amine, i.e. compound 18. The resulting benzyloxycarbonyl-protected intermediate, 7, was deprotected through hydrogenolysis. An additional aryl amine, 8, was prepared via the corresponding N-carbobenzyloxy protected intermediate 9.

Radioiodinated aryl amine derivatives have an advantage over radioiodinated phenols as molecular probes, in that they may be cross-linked to the receptor protein. Aryl amines, following iodination with $^{125}$I, have been photoaffinity crosslinked to A$_1$-adenosine receptors (Stiles et al., J. Biol. Chem., 260:10806-10811, 1985) or converted to azido derivatives which were photolyzed in the receptor-bound state (Stiles et al., J. Neurochem. Vol. 47, pp. 1020-1025, 1986; Linden et al., J. Med. Chem. 31:745-751, 1988). Compounds 6 and 8 are designed for both radioiodination and photo-affinity crosslinking. Compound 8 was designed in an attempt to overcome low yield in the iodination step (see below), due to possible oxidation at a benzylic methylene group of 6. Compound 8 is a benzoic acid derivative, in which one potentially susceptible α-methylene group is absent. The meta-aniline derivative was selected over the para-, because of its greater nucleophilicity (required for the cross-linking reaction) based on electronic effects and pKa data in 3-aminobenzoyl derivatives versus the corresponding 4-aminobenzoyl derivatives.

Figure 3:
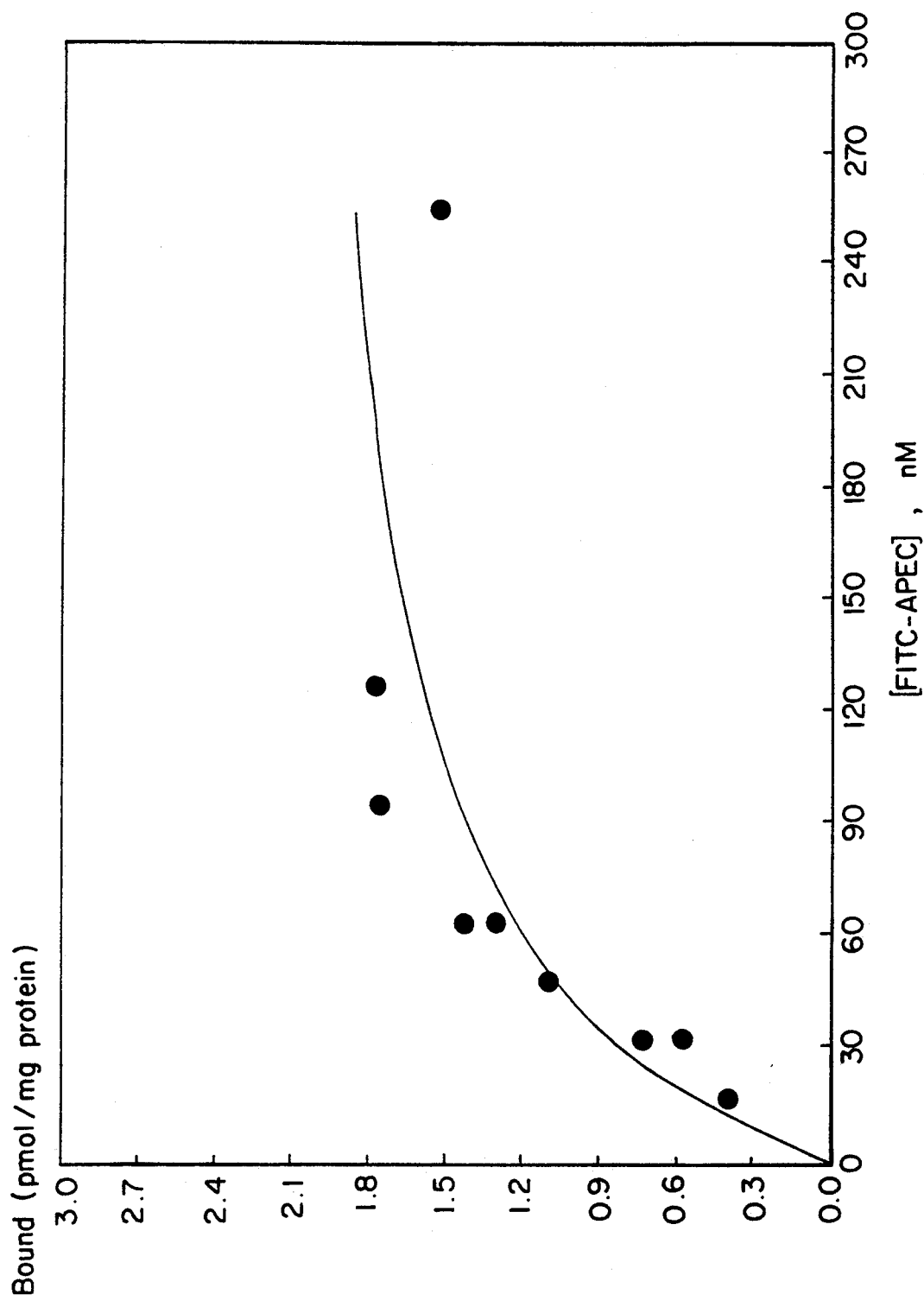
FIG. 3 is a saturation isotherm relating variable concentrations of FITC-APEC binding to bovine striatal membranes.

PAPA-APEC, 6, was radioiodinated by the chloramine T method in 70% radiochemical yield. The product, $^{125}$I-PAPA-APEC, having a specific activity of approximately 2200 Ci/mmol, was purified by reverse phase high pressure liquid chromatography (FIG. 3). The two main radioactive peaks were identified using TLC as $^{125}$I-PAPA-APEC (peak B) and recovered $^{125}$I-iodide. The major ultraviolet absorbing peak (A) corresponded to unreacted compound 6.

$^{125}$I-PAPA-APEC displayed a 60-80% degree of specific binding to striatal A$_2$-adenosine receptors in the bovine brain with a $K_d$-value of 1.4 nM (Barrington et al., 1989, supra) $^{125}$I-PAPA-APEC was used in photoaffinity cross-linking followed by SDS gel electrophoresis to determine the molecular weight of this receptor to be 45,000 (Barrington et al., 1989, supra).

A prosthetic group for radiofluorination of functionalized drugs and peptides was recently reported (Shai et al., Biochemistry, 28:4801-4806, 1989). This group consisted of a 4-fluoromethylbenzoyl moiety (FMB) obtained through nucleophilic fluorination (with $^{18}$F) of the corresponding 4-bromomethylbenzoyl derivatives. As a potential $^{18}$F probe for in vivo positron emission tomography of A$_2$-adenosine receptors, an FMB derivative of CGS21680 compound 16, in which the spacer chain consists of 1,4-diaminobutane, was prepared. It was synthesized by condensing the 4-[4-(fluoromethyl)-benzoylamino]butaneamine (Shai et al., 1989, supra) with CGS21680.

Non-radioactive Probes

APEC was acylated with other reporter groups suitable for non-radioactive methods of receptor characterization. Biotin-avidin technology has been used to isolate receptors by affinity chromatography on immobilized avidin columns (Finn et al., In Insulin Receptors, Part A, Alan R. Liss Publishers, pp. 3-14, 1988) and for histochemistry. A biotin conjugate of APEC, 10, was synthesized for this purpose.

The amine-functionalized congeners XAC and ADAC, which are antagonist and agonist probes, respectively, for A$_1$-receptors, have been converted to irreversibly binding ligands for the receptor (Stiles et al., 1988, supra; Jacobson et al., J. Med. Chem. Vol. 32, pp. 1043–1051, 1989(b)) through chemical activation using hetero- and homobifunctional cross-linking reagents. Examples of bifunctional reagents used successfully in that capacity are the p- and m- isomers of phenylenediisothiocyanate (DITC). m- and p-DITC-APEC, compounds 11 and 12, respectively, were synthesized as potentially chemically reactive affinity labels. A bromoacetyl N$^6$-substituted derivative of adenosine was found to inhibit A$_1$-adenosine receptors irreversibly (Jacobson et al., 1989(b), supra).

An additional thiourea derivative, 13, containing a sulfonate salt, was found to be more than 200-fold selective for A$_2$ receptors.

A spin label probe, compound 15, containing the stable free radical TEMPO (2,2,6,6-tetramethyl-1-piperidinyloxy), for detection using electron spin resonance spectroscopy (Blanton et al., Mol. Pharmacol. 33:634–642, 1988), was prepared from APEC and the isothiocyanate derivative of TEMPO. Fluorescent probes, compounds 17 and 18, derivatives of the fluorescent dyes fluorescein and NBD, respectively, also displayed high affinity at A$_2$-adenosine receptors and are useful in spectroscopic based binding assays.

which the A$_1$-selective ligand N$^6$-cyclopentyladenosine is added to eliminate the A$_1$-receptor component of specific binding, 2) inhibition of binding of [$^3$H]CGS21680 to rat striatal membranes, and 3) inhibition of binding of $^{125}$I-PAPA-APEC to bovine brain striatal membranes. Striatal membranes from the calf were used for the following reasons 1) Bovine striatum has a higher density of A$_2$-adenosine receptors than does the rat (1.1 vs. 0.5 pmol receptor per mg of protein). 2) Larger quantities of striatum are more readily dissected from calf brains than from rat brains. 3) Bovine A$_2$-receptors are more stable to storage and have more favorable levels of non-specific binding of radioligands.

At A$_2$-adenosine receptors the derivatives retained high affinity, comparable to CGS21680, from which they were prepared. CGS21680 had a K$_i$-value of 14 nM in inhibition of binding of $^{125}$I-PAPA-APEC Compounds 2, 3, 7, 9, 11, and 12 displayed K$_i$-values less than 10 nM in displacement of binding of $^{125}$I-PAPA-APEC from bovine brain A$_2$-adenosine receptors. Compounds 6, 8, and 16 were less potent in displacing $^{125}$I-PAPA-APEC binding.

Table 2 summarizes the data hereinbelow.

TABLE 2

Potencies of adenosine derivatives and xanthines at adenosine A$_1$ and at A$_2$-adenosine receptors in binding assays.[a]

| | ligand: | | | | |
|---|---|---|---|---|---|
| | A$_1$-receptors | A$_2$-receptors | | | |
| | [$^3$H]PIA | $^{125}$I-PAPA-APEC | [$^3$H]NECA | [$^3$H]CGS21680 | |
| | | species: | | | |
| Compound | rat | bovine | rat | rat | K$_i$(A$_1$)/K$_i$(A$_2$)[e] |
| NECA | 6.26 ± 0.52[b] | 55 ± 26 | 10.3 ± 0.5[b] | 12 ± 1 | 0.11 |
| R-PIA | 1.17 ± 0.16[b] | 870 ± 270 | 120[b] | 410 ± 32 | 0.0013 |
| S-PIA | 49.3 ± 2.4[b] | 10,300 ± 2800 | 1820 ± 380[b] | 3020 ± 210 | 0.0048 |
| ADAC | 0.85 | d | 210 | 218 ± 28 | — |
| theophylline | 8470 ± 1490[b] | 20,300 ± 2700 | 25,300 ± 2000[b] | 20,800 ± 1540 | 0.417 |
| XAC | 1.2 ± 0.5 | d | 70 | 30.7 ± 1.7 | — |
| 1 | 2600 ± 300[c] | 14.1 ± 2.1 | 15 | 14 ± 1 | 184 |
| 2 | 2260 ± 440[c] | 6.1 ± 1.5 | 17.5 ± 1.6 | 5 ± 2 | 370 |
| 3 | 235 ± 54 | 6.1 ± 1.3 | 5.73 ± 0.52 | 12 ± 3 | 16 |
| 4 | 950 ± 100[c] | 13.2 ± 1.5 | d | 13 ± 4 | 72 |
| 5 | 1400 ± 100[c] | 21.3 ± 7.9 | d | 15 ± 1 | 66 |
| 6 | 1340 | 43 ± 14 | d | 28 ± 7 | 31 |
| 7 | 278 ± 18.7 | 6.2 ± 0.9 | 5.59 ± 0.99 | 37 ± 5 | 45 |
| 8 | 1340 ± 28 | 43.6 ± 5.2 | d | 16.5 ± 2.8 | 31 |
| 9 | 680 ± 110[c] | 8.7 ± 2.0 | d | 12 ± 2 | 78 |
| 10 | >5000[c] | 14.3 ± 3.3 | d | 55 ± 30 | >350 |
| 11 | 69.7 ± 7.9 | 6.2 ± 2.1 | 2.82 ± 0.38 | 22 ± 7 | 11 |
| 12 | 276 ± 75[c] | 7.1 ± 2.3 | d | 35 ± 10 | 39 |
| 13 | 3780 ± 800 | 10.9 ± 2.3 | d | 26 ± 10 | 347 |
| 14 | 1980 ± 102 | 15.8 ± 4.8 | d | 69.7 | 125 |
| 15 | 177 ± 38[c] | 14.8 ± 3.6 | d | 27 ± 3 | 12 |
| 16 | 1450 ± 67 | 25.4 ± 7.6 | d | 18.9 ± 4.9 | 57 |
| 17 | d | 31.6 ± 1.3 | d | d | — |
| 18 | d | 59.8 ± 28 | d | d | — |

[a]unless noted, expressed as the K$_i$-value in nM, for inhibition of binding of [$^3$H]PIA at A$_1$ receptors, inhibition of binding of $^{125}$I-PAPA-APEC, [$^3$H]NECA, or [$^3$H]CGS21680 at A$_2$ receptors. Compounds 11, 12, and 14 are potential irreversible inhibitors of A$_2$ receptors, thus the values given represent apparent K$_i$'s. Values are the means ± s.e.m. for three or more determinations done in triplicate. The A$_2$ selectivity ratio derived from Ki-values for $^{125}$I-PAPA-APEC binding at A$_2$ receptors.
[b]data from Bruns et al, 1986, inhibition of binding of [$^3$H]N$^6$-cyclohexyladenosine at A$_1$ receptors, inhibition of binding of [$^3$H]NECA at A$_2$ receptors.
[c]using [$^3$H]N$^6$-cyclohexyladenosine.
[d]not determined.
[e]the ratio of Ki values at A$_1$-receptors versus the Ki values in the $^{125}$I-PAPA-APEC assay.

Assays of Receptor Affinity and Adenylate Cyclase

The adenosine analogs were assayed for affinity at A$_1$-adenosine receptors using the radioligands [$^3$H]N$^6$-phenylisopropyladenosine and [$^3$H]N$^6$-cyclohexyladenosine. At A$_2$-receptors, three methods were used for comparison: 1) inhibition of binding of [$^3$H]5'-N-ethylcarboxamidoadenosine to rat striatal membranes, according to the method of Bruns et al., 1986, supra, in

Biological Activity of the Adenosine Agonists

The ability of compound 6 to increase cyclic AMP in human platelets according to the procedure of (Newman et al., 1978, supra) is shown in FIG. 1. A dose dependent increase in cyclic AMP was observed (FIG. 1) over the range of concentration of compound 6 of 1 nM to 10 μM. At $10^{-6}$M compound 6 produced a 40% increase in the level of cyclic AMP. At the same concentration NECA produced a comparable 35% rise in cyclic AMP.

Compounds useful in fluorescent binding assays of adenosine $A_2$ receptors in striatal membranes may be used to screen new ligands for affinity at these receptors, thus contributing to the development of new drugs specific or selective to this receptor. Currently the only other methods for assaying binding at these receptors requires the use of other types of radioactive tracers (Bruns et al., *Mol. Pharmacol.*, Vol. 29, pp. 331-346, 1986 and Jarvis et al., *J. Pharmacol. Exp. Therap.*, Vol. 251, pp. 888-893, 1989). The following is an example.

EXAMPLE 18

Fluorescent Studies

Tissue Preparation

Striatal tissues obtained from bovine brain (Pel-Freeze, Biologicals, Rogers, Ark.) were homogenized in 10 volumes of 0.32M sucrose using a Teflon pestle and glass tube (6-7 passes). The homogenate was centrifuged (4° C.) at 579×g (2,000 rpm) for 10 minutes 4° C.). The initial pellet ($P_1$) was discarded and supernatant recentrifuged at 4° C. (16,000 rpm) for 1 hour. The resultant pellet ($P_2$) was resuspended in ice-cold distilled water using a Brinkman Polytron (setting 6-7, for 3 seconds) and centrifuged (4° C.) at 37,059×g for 1 hour. The distilled water supernatant was decanted and the pellet was resuspended in buffer (50 mM TrisHCl, pH 7.4 at 4° C.) and centrifuged a final time for 1 hour. Tissue homogenates were tested at −80° C. for 1-3 days until binding assays were performed. Adenosine deaminase, (Boehringer Mannheim Biochemicals, Indianapolis, Ind.) from calf intestine was included (10 μ/mg protein, specific activity=200μ/mg) in the incubation media to eliminate endogenous adenosine. Protein quantities were assessed by using the Pierce BCA Protein Assay Reagent (Rockford, Ill.). Protein quantities were ∼300μg/assay tube.

FITC-APEC Binding

Fluorescence intensity (counts per second, cps) was measured using a SPEX Fluorolog Model 1680 0.22-m Double Spectrometer with DM3000 software (SPEX Industries, Edison, N.J.). Excitation and emission spectra were determined by comparing FITC-APEC (Compound 18, 1 μM) to buffer (50 nM Tris.HCl containing 10 nM $MgCl_2$, pH 7.4 or 8.1 at room temperature) or tissue suspension equivalent in concentration to that used for fluorescent ligand binding experiments. Excitation and emission maxima for FITC-APEC were 492 and 516 nm, respectively. These values were not significantly altered by different buffer composition or temperature.

Association studies of FITC-APEC were performed by incubating (room temperature) striatal membranes in polypropylene tubes containing buffer (pH 7.4) and FITC-APEC (50 nM) for 5-120 minutes. The 1 ml incubation media consisted of 700 μl buffer, 100 μl striatal tissue suspension (typically 300 μg protein per assay), 100 μl FITC-APEC (50 nM), and 100 μl 2-chloroadenosine (Research Biochemicals, Inc. Natick, Mass.) or buffer. The 2-chloroadenosine was used to define nonspecific binding. Following each incubation interval, reactions were terminated by centrifugation (4° C.) at 20,000×g (14,000 rpm) for 20 minutes in a Hermle Z360K centrifuge (Berthold Hermle GmbH Co., Gosheim, FRG). The pellets were rinsed superficially with 2×1-ml aliquots of buffer (pH 7.4). The portion of each assay tube containing the tissue pellet was cut and transferred to polystyrene cuvettes (Sarstedt, Newton, N.C.). Subsequently, tissues were resuspended in 1 ml of buffer (pH 8.1, plus 1 μM 2-chloroadenosine).

Saturation isotherms were constructed from data obtained by incubating (room temperature) bovine striatal membranes for 90 minutes in the presence variable concentrations (16-256 nM) of FITC-APEC. The binding parameters used were similar to those described for the association studies.

Quantitation (see McCabe et al. *Faseb J.*, Vol. 4, pp 2934-2945, 1990) of FITC-APEC binding was performed by generating a standard line relating fluorescence intensity (cps) emitted to known concentrations (0.5-1024 nM) of FITC-APEC, in buffer ("free" ligand) or tissue suspension.

Results

Bound ligand concentrations (μM) were estimated using linear regression analysis and mole quantities of FITC-APEC bound/mg protein were subsequently determined.

The binding of FITC-APEC to membrane preparations of bovine striatum reached equilibrium by 90 minutes (FIG. 1A). Thus, a 90 minute incubation (room temperature) period was used in all other fluorescent ligand binding assays.

FITC-APEC binding to bovine striatal membranes was saturable as illustrated by an isotherm representing bound ligand versus increasing concentrations of FITC-APEC (FIG. 1B). The $K_d$ and $B_{max}$ values were 54.6 nM and 2.26 pmol/mg protein, respectively. These data were consistent with previous results for this series of 2-substituted adenosine functionalized congeners using radioligand binding techniques Furthermore, displacement of $^{125}$I-APNEA from bovine striatum $A_2$ adenosine receptors using FITC-APEC yielded a $K_i$ value of 59.8±28 nM.

The above-cited properties are demonstrable in in vitro and in vivo tests, using advantageously mammals, e.g. rats, dogs, monkeys or isolated organs, tissues and preparations thereof. Said compounds can be administered in vitro in the form of solutions, e.g. preferably aqueous solutions, and administered in vivo either enterally or parenterally advantageously orally or intravenously, e.g. within gelatin capsules, as starch suspensions or in aqueous solutions.

The appropriate dosage in vitro may range between about $10^{-5}$ molar and $10^{-9}$ molar concentrations. The dosage in vivo may range between about 0.001 and 25 mg/kg/day, preferably between about 0.0025 and 10 mg/kg/day depending on the compound and the route of administration.

Typically, the blood pressure lowering effect in normotensive rats can be determined as follows:

Adult male rats weighing 300-400 g are anesthetized using Inactin (100 mg/kg, i.p.). A femoral artery and contralateral vein are cannulated for direct blood pressure measurement and i.v. drug administration, respectively. Animals are allowed a 15 minute equilibration period before testing. Vehicle (1 ml/kg, i.v.) is administered over a 30 second period followed by a 0.3 ml saline flush administered over a 30 second period. Changes in diastolic blood pressure are recorded using a Beckman polygraph while heart rate is recorded as a derivative of the blood pressure pulse. The test compound is administered in the same manner as vehicle and a dose response curve is established. Percent changes in heart rate and blood pressure are recorded.

The blood pressure lowering effect in the spontaneous hypertensive rat is determined on oral administration as known in the art.

Antithrombotic activity can be demonstrated e.g. by measuring the inhibition of collagen-induced platelet aggregation.

Illustrative compounds of the invention have an $IC_{50}$ of about $1 \times 10^{-7}M$ in the in vitro adenosine-2 receptor binding assay, and effectively lower blood pressure at a dose of about 10 mg/kg p.o. in the spontaneous hypertensive rat model. They also demonstrate in vitro activity indicative of more than 100 fold greater potency at the $A_2$ receptor than at the $A_1$ receptor.

The present invention also relates to the use of the compounds of the invention for the preparation of pharmaceutical compositions, especially pharmaceutical compositions having adenosine-$A_2$ agonist activity which can be used for the treatment of e.g. central nervous system disorders, cardiovascular conditions, such as hypertension, thrombosis and atherosclerosis.

The pharmaceutical compositions according to the invention are those suitable for enteral, such as oral or rectal, transdermal and parenteral administration to mammals, including man, for the treatment of diseases responsive to adenosine-$A_2$ agonist activity, such as hypertension, comprising an effective adenosine-$A_2$ stimulating amount of a compound of the invention, alone or in combination with one or more pharmaceutically acceptable carriers.

The pharmacologically active compounds of the invention are incorporated into pharmaceutical compositions comprising an effective amount thereof in conjunction or admixture with excipients or carriers suitable for either enteral or parenteral application. Preferred compositions are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethylene glycol; for tables also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The present invention also relates to the use of compounds of the invention having adenosine-$A_2$ agonist properties and pharmaceutical compositions comprising said compounds of the treatment in mammals of disorders responsive to adenosine-$A_2$ agonist activity particularly cardiovascular conditions which include e.g. hypertension and thrombosis.

One aspect relates advantageously to a method of enhancing adenosine-$A_2$ agonist activity in mammals and to the method of treating cardiovascular disorders in mammals, e.g. such responsive to adenosine-2 agonist activity, for example hypertension or thrombosis using an antihypertensive effective amount of an antithrombocytic effective amount of a compound of the invention, preferably in the form of the above-cited pharmaceutical compositions.

The dosage of active compound administered is dependent of the species of warm-blooded animal (mammal), the body weight, age and individual condition, and on the form of administration.

A unit dosage for a mammal of about 50 to 70 kg may contain between about 5 and 100 mg of the active ingredient.

EXAMPLE 19

Preparation of 10,000 tablets each containing 20 mg of the active ingredient:

| Formula: | |
|---|---|
| APEC | 200.00 g |
| Lactose | 2,400.00 g |
| Corn starch | 125.00 g |
| Polyethylene glycol 6,000 | 150.00 g |
| Magnesium stearate | 40.00 g |
| Purified water | q.s. |

Procedure

All the powders are passed through a screen with openings of 0.6 mm. Then the drug substance, lactose, magnesium stearate and half of the starch are mixed in a suitable mixer. The other half of the starch is suspended in 65 ml of water and the suspension is added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

b) Preparation of 1,000 capsules each containing 20 mg of the active ingredient:

| Formula: | |
|---|---|
| APEC | 20.0 g |
| Lactose | 197.0 g |
| Modified starch | 80.0 g |
| Magnesium stearate | 3.0 g |

Procedure

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

EXAMPLE 20

Locomotor Depression by $A_2$ Adenosine Agonists

Individual NIH mice (25-30 g) were studied in a Digiscan activity monitor (Omnitech Electronics Inc., Columbus, Ohio) equipped with an IBM-compatible computer. Data is collected in the morning, for three consecutive intervals of 10 min each and analyzed as a group for 30 min sampling period. All drugs are dissolved in a 1:4 v/v mixture of Emulphor EL-620 (GAF Chemicals Corp., Wayne, N.J.) and phosphate buffered saline and administered i.p. in a volume of 5 ml/kg b.w. Warming and sonication aid in dissolving the drugs. When appropriate, an adenosine antagonist is injected first followed by an agonist after 10 min. Immediately after the final injection, the mouse is placed in the activity monitor cage, and data collection is begun after a delay of 10 min. Statistical analysis is performed using the Student T test. Each value reported represents the mean±s.e.m. for 6 to 10 animals, except for the control points (vehicle injected) for which n=22.

APEC, 3, proved to be a potent locomotor depressant in mice in a dose-dependent manner. The in vivo pharmacology was consistent with $A_2$-selectivity at a central site of action. Two parameters indicative of locomotor activity, horizontal activity and total distance traveled, were measured. From dose response curves it was found that APEC (ED50 16 µg/kg) is more potent than CHA ($N^6$-cyclohexyladenosine) (ED50 60 µg/kg) and less potent than NECA (ED50 2 µg/kg). The locomotor depression by APEC was reversible by theophylline (at the ED50 dose of APEC, 10 mg/kg theophylline restore the total distance traveled to 95±12% of control), but not by the $A_1$-selective antagonists 8-cyclopentyltheophylline (10 mg/kg) and 8-cyclopentyl-1,3-dipropyl-2-thioxanthine, nor by the peripheral antagonists 8-p-sulfophenyltheophylline and 1,3-dipropyl-8-p-sulfophenylxanthine. The locomotor activity depression elicited by NECA and CHA was reversed by $A_1$-selective antagonists. Thus, the effects of APEC are due to stimulation of $A_2$ adenosine receptors in the brain.

Other of the $A_2$-selective adenosine derivatives were found to elicit the following degrees of locomotor depression (% decrease in horizontal activity from vehicle control) at the doses of 160 µg/kg: compound 4, 44±7%; compound 5, 49±9%; compound 13, 41±5%; and compound 16, 50±4%.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A compound having the formula

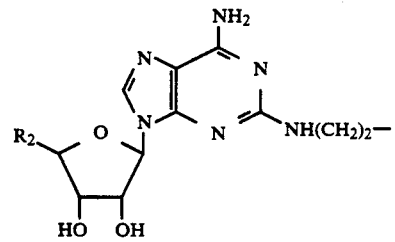

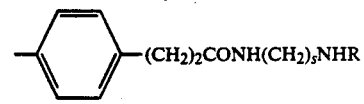

wherein
R is H, $C_1$-$C_7$ lower alkyl, $C_1$-$C_7$ lower alkenyl, an acyl radical of the formula R—C(O)—, an isothiocyanate radical, or a reporter group; and
$R^2$ is $(CH_2)_nOH$ or $CONH(CH_2)_nH$ or CONH-cyclopropyl wherein n=1-4, and wherein s=1-6, or a physiologically acceptable salt thereof.

2. The compound according to claim 1 having the formula

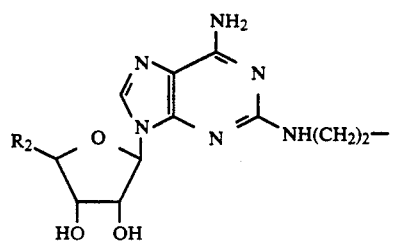

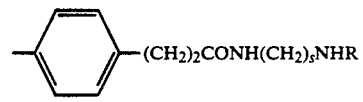

wherein
R is H, $C_1$-$C_4$ lower alkyl, $C_1$-$C_4$ lower alkenyl,

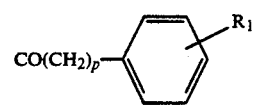

and wherein
$R_1$=OH, $NH_2$, $NHCO_2CH_2C_6H_5$, $(CH_2)_mX$, m=0-4,
X=Cl, F, or Br, and p=0-4,

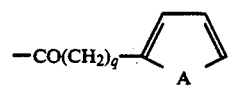

and wherein A=0 or S, and q=0-4, $CO(CH_2)_nX$,

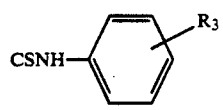

wherein $R_3$ is NCS or $SO_3Na$; or a reporter group; and
$R_2$ is $(CH_2)_nOH$ or $CONH(CH_2)_nCH_3$ or CONH-cyclopropyl
wherein n=1-4; or a physiologically acceptable salt thereof.

3. The compound according to claim 2 wherein said reporter group is selected from the group consisting of a spectroscopic reporter group, a fluorescent dye, a chemical or photochemical affinity probe and a spin label probe.

4. The compound according to claim 2 wherein R is a radiolabeled prosthetic group.

5. The compound according to claim 3 wherein said fluorescent dye is selected from the group consisting of 5- (and 6-)-carboxynaphthofluorescein, 5-(and 6-) carboxyfluorescein 7-hydroxycoumarin-4-acetic acid, acridone-10-acetic acid, tetramethylrhodamine-5-(and-6)-isothiocyanate (TRITC), 1-pyreneisothiocyanate, 9-acridineisothiocyanate, and 4,4'-diisothiocyanatostilbene-2,2'-disulfonic acid, disodium salt (DIDS).

6. The compound of claim 3 wherein said spin label probes are selected from the group consisting of 4-isothiocyanate-2,2,6,6,-tetramethyl piperidinyloxy free radical, N-(4-(iodoacetyl)amino)-2,2,6,6-tetramethyl-piperidine-1-oxyl (TEMPO 1A), N-(3-(iodoacetyl-)amino)-2,2,5,5-tetramethylpyrrolidine-1-oxyl (PROXYL 1A), succinimidyl 2,2,5,5-tetramethyl-3-pyrroline-1-oxyl-3-carboxylate, 2,2,5,5-tetramethyl-3-pyrroline-1-oxyl-3-carboxylic acid, and 9-doxylstearic acid.

7. The compound of claim 6 wherein said spin label probe is 4-isothiocyanate-2,2,6,6-tetramethyl piperidinyloxy free radical.

8. The compound according to claim 3 wherein said photoaffinity probe is selected from the group consisting of bromoacetyl, m- or p-phenylenediisothiocyanate, N-succinimidyl suberic acid, 4-azidosalicylic acid, 2-(p-azidosalicylamido)ethyl-1,3'dithiopropionic acid, 5-azido-2-nitrobenzoic acid, 2-(m-azido-o-nitrobenzamido)ethyl-1,3'dithiopropionic acid, 6-(4'-azido-2'-nitrophenylamino)hexanoate, (4-azidophenyl)-1,3'-dithiopropionic acid, 4-azidobenzoic acid, 4-azidophenylisothiocyanate, 2-diazo-3,3,3-trifluoropropionic acid.

9. The compound according to claim 4 wherein said radiolabeled compound is selected from the group consisting of diethylenetriaminepentacetic acid, ethylenediamine tetraacetic acid, 2-p-nitrobenzyl-1,4,7,10-tetraazacyclododecane-N,N',N'',N'''-tetraacetic acid, dimercaptosuccinate, N,N'-1,2-ethylenediylbis-L-cysteine diethyl ester, p-hydroxyphenylpropionic acid, p-aminobenzoic acid.

10. A pharmaceutical composition comprising an effective amount of the compound according to claim 2 having the formula

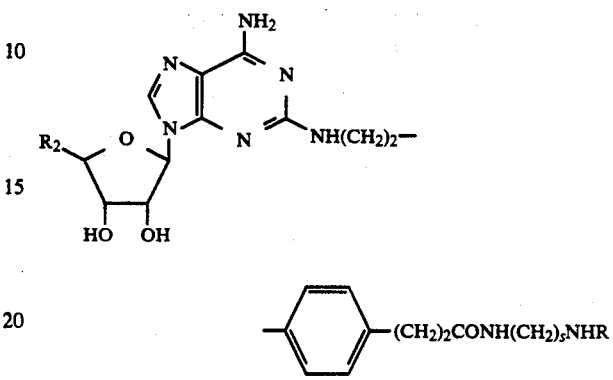

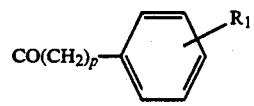

wherein
R is H, $C_1$-$C_4$ lower alkyl, $C_1$-$C_4$ lower alkenyl,

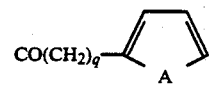

and
$R^1$ is H, OH, $NH_2$, $NHCO_2CH_2C_6H_5$, $(CH_2)_mX$, wherein m=0-4, X=Cl, Br or F, wherein p=0-4, $CO(CH_2)_q$—A and
A is O, or S, q=0-4; and
$R_2$ is $(CH_2)_nOH$, $CONH(CH_2)_nH$ and n=1-4, or a physiologically acceptable salt thereof; and a pharmaceutically acceptable carrier.

* * * * *